*(12)* United States Patent
Van Der Ley et al.

(10) Patent No.: US 6,482,807 B1
(45) Date of Patent: Nov. 19, 2002

(54) LPS WITH REDUCED TOXICITY FROM GENETICALLY MODIFIED GRAM NEGATIVE BACTERIA

(75) Inventors: Peter Andre Van Der Ley, Utrecht (NL); Hendrik Jan Hamstra, Wijk Bij Duurstede (NL); Liana Juliana Josephine Margriet Steeghs, Utrecht (NL)

(73) Assignee: De Staat Der Nederlanden, vertegenwoordigd door de minister van welzijn, Volksgezondheid en Cultuur, Rijswijk (NL)

( * ) Notice: Subject to any disclaimer, the term of this patent is extended or adjusted under 35 U.S.C. 154(b) by 0 days.

(21) Appl. No.: 09/830,910
(22) PCT Filed: Nov. 3, 1998
(86) PCT No.: PCT/NL98/00633
§ 371 (c)(1),
(2), (4) Date: Jul. 2, 2001
(87) PCT Pub. No.: WO00/26384
PCT Pub. Date: May 11, 2000
(51) Int. Cl.$^7$ ................................................. A01N 43/04
(52) U.S. Cl. .......................... 514/54; 514/25; 536/17.2; 536/123.13
(58) Field of Search .................... 514/25, 53; 536/17.2, 536/123.13

(56) References Cited

FOREIGN PATENT DOCUMENTS

| WO | WO 9719688 | 6/1997 |
|---|---|---|
| WO | WO 9725061 | 7/1997 |

OTHER PUBLICATIONS

Lee et al, Journal of Biological Chemistry, vol. 270, No. 45, Nov. 10, 1995, pp. 27151–27159.*

Hone et al, Journal of Human Virology, vol. 1, No. 4, May 1998, p. 251–256.*

Clementz et al, Journal of Biological Chemistry, vol. 272, Apr. 18, 1997, pp. 10353–10360.*

* cited by examiner

*Primary Examiner*—James O. Wilson
*Assistant Examiner*—Vanessa Ford
(74) *Attorney, Agent, or Firm*—Handal & Morofsky (57) ABSTRACT

The subject invention lies in the field of vaccines. Specifically new compounds that can be used as adjuvants are provided. Recombinant LPS having a reduced number of secondary acyl chains per molecule of LPS vis a vis the corresponding non modified LPS molecule, said secondary acyl chains being bound to primary acyl chains, said primary acyl chains being bound to the glucosamine of said recombinant LPS molecule, said recombinant LPS being homogenous in acylation pattern is an example of such a compound. Also recombinant LPS having a phosphate group attached to the glucosamine at the non reducing end of the LPS molecule and a phosphate group attached to the glucosamine at the reducing end of the molecule per recombinant LPS molecule provides a further example.

9 Claims, 8 Drawing Sheets

Fig 3 htrB1 sequence
1293 bp

Fig 2b(1)

```
1         10        20        30        40        50
CGGGCCCCCCCTCGAGGTCAACGTCAATCCGGCATCGACGCTGATGCTCG
  G  P  P  L  E  V  N  V  N  P  A  S  T  L  M  L

GTCAGGCTAGGGGCGCGGCATTGGCGGCATTGGTCAGCCATAAGCTGCCC
  G  Q  A  R  G  A  A  L  A  A  L  V  S  H  K  L  P

GTTTCGGAATACACGGCCTTGCAGGTCAAACAGGCGGTAGTCGGCAAGGG
  V  S  E  Y  T  A  L  Q  V  K  Q  A  V  V  G  K

CAAGGCGGCAAAAGAACAGGTGCAGCATATGGTGGTGCAGATGTTGGGAC
  G  K  A  A  K  E  Q  V  Q  H  M  V  V  Q  M  L  G

TTTCGGGAACGCCCCAGCCGGATGCGGCGGACGGTCTTGCCGTCGCGCTG
  L  S  G  T  P  Q  P  D  A  A  D  G  L  A  V  A  L
                                                    primer 670-1
ACCCACGCCTTACGCAACCACGGGCTTGCCGCCAAACTCAATCCTTCGGG
  T  H  A  L  R  N  H  G  L  A  A  K  L  N  P  S
                                        stop ruvC gene
GATGCAGGTCAAGCGCGGCAGGTTTCAATAGTTTCAGACGGCATTTGTAT
  G  M  Q  V  K  R  G  R  F  Q  -
                              start htrB1 gene
TTTGCCGTCTGAAAAGAAAATGTGTATCGAGATGAAATTTATATTTTTG
                       M  C  I  E  M  K  F  I  F  F TACTGTATGTTTTGCAGTTTCTGCCGTTTGCGCTGCTGCACAAGATTGCC
  V  L  Y  V  L  Q  F  L  P  F  A  L  L  H  K  I  A GACCTGACGGGTTTGCTTGCCTACCTTCTGGTCAAACCGCGCCGCCGGAC
  D  L  T  G  L  L  A  Y  L  L  V  K  P  R  R  R CGGCGAAATCAATTTGGCAAAATGTTTTTCCGAATGGAGTGAGGAAAAGC
  T  G  E  I  N  L  A  K  C  F  S  E  W  S  E  E  K GTAAAACCGTGTTGAAACAGCATTTCAAACACATGGCGAAACTGATGTTG
  R  K  T  V  L  K  Q  H  F  K  H  M  A  K  L  M  L GAATACGGTTTATATTGGTACGCGCCTGCCGGACGTTTGAAATCGCTGGT
  E  Y  G  L  Y  W  Y  A  P  A  G  R  L  K  S  L GCGCTACCGCAATAAGCATTATTTGGACGACGCGCTGGCGGCGGGGGAAA
  V  R  Y  R  N  K  H  Y  L  D  D  A  L  A  A  G  E
```

Fig 2b(2)

```
AAGTCATCATCCTGTATCCGCACTTCACCGCGTTCGAGATGGCGGTGTAC
 K   V   I   I   L   Y   P   H   F   T   A   F   E   M   A   V   Y

GCGCTTAATCAGGATATCCCGCTGATCAGTATGTATTCCCATCAAAAAA
 A   L   N   Q   D   I   P   L   I   S   M   Y   S   H   Q   K
                            primer 447-2
CAAGATATTGGACGAACAGATTTTGAAAGGCCGCAACCGCTATCACAACG
 N   K   I   L   D   E   Q   I   L   K   G   R   N   R   Y   H   N TCTTCCTTATCGGGCGCACCGAAGGGCTGCGCGCCCTCGTCAAACAGTTC
 V   F   L   I   G   R   T   E   G   L   R   A   L   V   K   Q   F CGCAAAAGCAGCGCGCCGTTTCTGTATCTGCCCGATCAGGATTTCGGACG
 R   K   S   S   A   P   F   L   Y   L   P   D   Q   D   F   G CAACGATTCGGTTTTTGTGGATTTTTTCGGTATTCAGACGGCAACGATTA
 R   N   D   S   V   F   V   D   F   F   G   I   Q   T   A   T   I CCGGATTGAGCCGCATTGCCGCGCTTGCAAATGCAAAAGTGATACCCGCC
 T   G   L   S   R   I   A   A   L   A   N   A   K   V   I   P   A ATTCCCGTCCGCGAGGCAGACAATACGGTTACATTGCATTTCTACCCTGC
 I   P   V   R   E   A   D   N   T   V   T   L   H   F   Y   P TTGGAAATCCTTTCCGGGTGAAGACGCGAAAGCCGACGCGCAGCGCATGA
 A   W   K   S   F   P   G   E   D   A   K   A   D   A   Q   R   M ACCGTTTTATCGAAGACAGGGTGCGCGAACATCCGGAACAATATTTTTGG
 N   R   F   I   E   D   R   V   R   E   H   P   E   Q   Y   F   W CTGCACAAGCGTTTTAAAACCCGTCCGGAAGGCAGCCCCGATTTTTACTG
 L   H   K   R   F   K   T   R   P   E   G   S   P   D   F   Y
                                                     stop htrB1 gene
ACTACGTAAAATTACAAAACATATCAGGCGTTTCAGATCAAAA
```

LPS WITH REDUCED TOXICITY FROM GENETICALLY MODIFIED GRAM NEGATIVE BACTERIA

This application is a 371 of PCT/NL98/00633 Nov. 3, 1998.

BACKGROUND TO THE INVENTION

The subject invention lies in the field of vaccines and more specifically provides novel compounds that can be used as adjuvants in vaccines. Many adjuvants have been described e.g. Freund type mineral oil emulsions, aluminium salts, saponins, muramyl dipeptide and derivatives MPL, MF59 etc. However only a few have actually been licensed for use in humans. This is generally due to an unfavorable ratio between immunostimmulatory action versus toxicity. A general reference concerning adjuvants can be found in The Theory and Practical Application of Adjuvants (D.E.S. Stewart-Tull ed. John Wiley & Sons 1995) and the information therein is incorporated by reference. The prior art also teaches for a number of organisms that enzymatic treatment of LPS can lead to reduced toxicity. The LPS illustrated as having undergone such treatment are: Salmonella typhimurium and Salmonella minnesota. The following are also suggested to exhibit such: all Gram negative bacteria and specifically Salmonella, Escherichia, Haemophilus, Moraxella, Campylobacter and Neisseria. Nowhere however are details provided concerning proof of adjuvant activity.

Looking at this prior art in detail shows that Munford et al (in U.S. Pat. No. 4,929,604 issued in 1990) show S typhimurium LPS in which 95% of secondary acyl groups have been removed through enzymatic treatment. The Munford treatment cannot specifically remove secondary acyl chains ensuring only partial deacylation. The Munford method cannot provide uniform product at best nearly all secondary acyl groups will be removed.

They suggest adjuvant activity could be present due to B cell mitogenicity testing. B cell mitogenicity testing however is not a reliable test to indicate adjuvant activity. It is probable that such product will not exhibit adjuvant activity. The Munford method in fact only shows removal of secondary acyl chains from the non reducing end of LPS. The resulting product does not contain any secondary acyl group on the reducing end of the LPS. The Munford product lacks both myristoyl and lauroyl secondary side chains. The Munford method cannot specifically remove only myristoyl or only lauroyl. The Munford method cannot remove only secondary acyl chain from one specific location. The Munford method is suggested to also be applicable to Escherichia, Haemophilus and Neisseria.

They show a Salmonella LPS with one phosphate group on the non reducing end and one on the reducing end. The Salmonella LPS has 1 myristoyl and 1 lauroyl group on the non reducing end. The Salmonella LPS has no secondary acyl group on the reducing end.

Myers et al in U.S. Pat. No. 4,912,094 use alkaline hydrolysis under controlled conditions to remove only the beta-hydroxymyristic acyl residue that is ester linked to the reducing end glucosamine at position 3. Thus a product in which one of the primary acyl chains has been chemically removed is described. Nothing is mentioned vis a vis secondary acyl chain removal. The resulting product is stated to be less toxic and maintains antigenic properties. This is merely stated based on reduced mitogenicity of MPL A (acid hydrolyzed) vis a vis B cell proliferation for the deacylated version. B cell mitogenicity testing however is not a reliable test to indicate adjuvant activity. Escherichia coli and Salmonella minnesota LPS are given as examples. Only biological activity data are however given for the Salmonella minnesota LPS. They suggest the method to be applicable to all LPS but offer no support thereof.

The same subject matter is discussed in an article of Erwin et al with Munford as co-author (1991). Quoting from the abstract of the Erwin article itself the following is remarked in the abstract "These studies indicate that the contribution of secondary acyl chains to the bioactivities of a given LPS cannot be predicted with confidence from the reported structure-activity relationships of Lipid A or from the behavior of other deacylated LPS."

Figure 1:
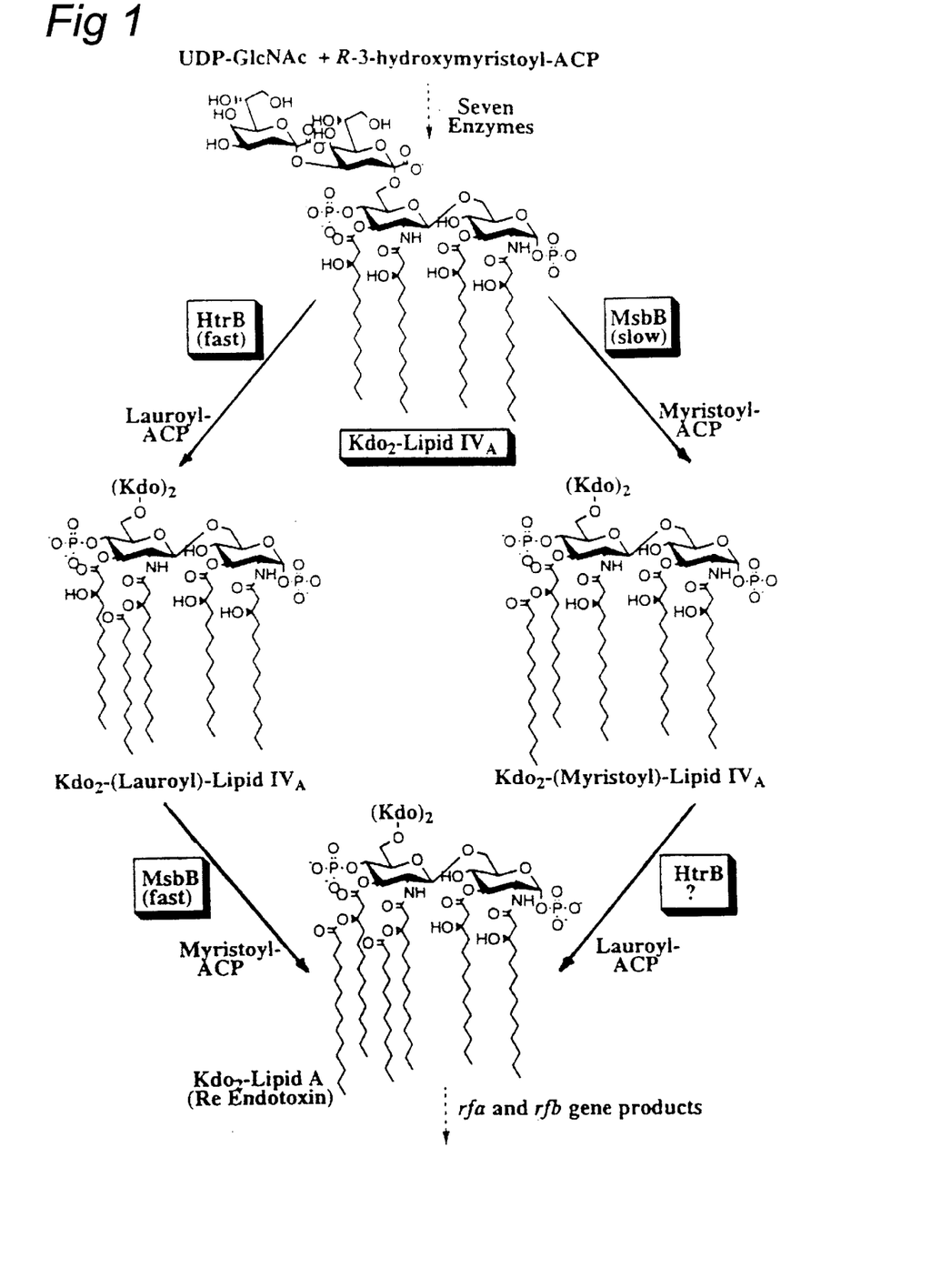
FIG. 1. Role of the htrB and msbB gene products in *Escherichia coli* lipid A biosynthesis FIG. 2. Organization (A) and sequence (B) of the htrB1 gene from *Neisseria, meningitidis*
Figure 2A:
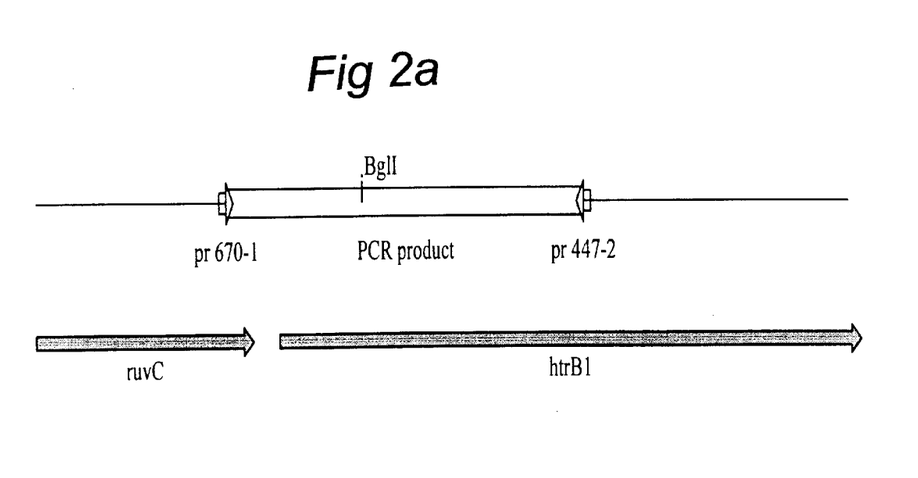
Figure 2B:
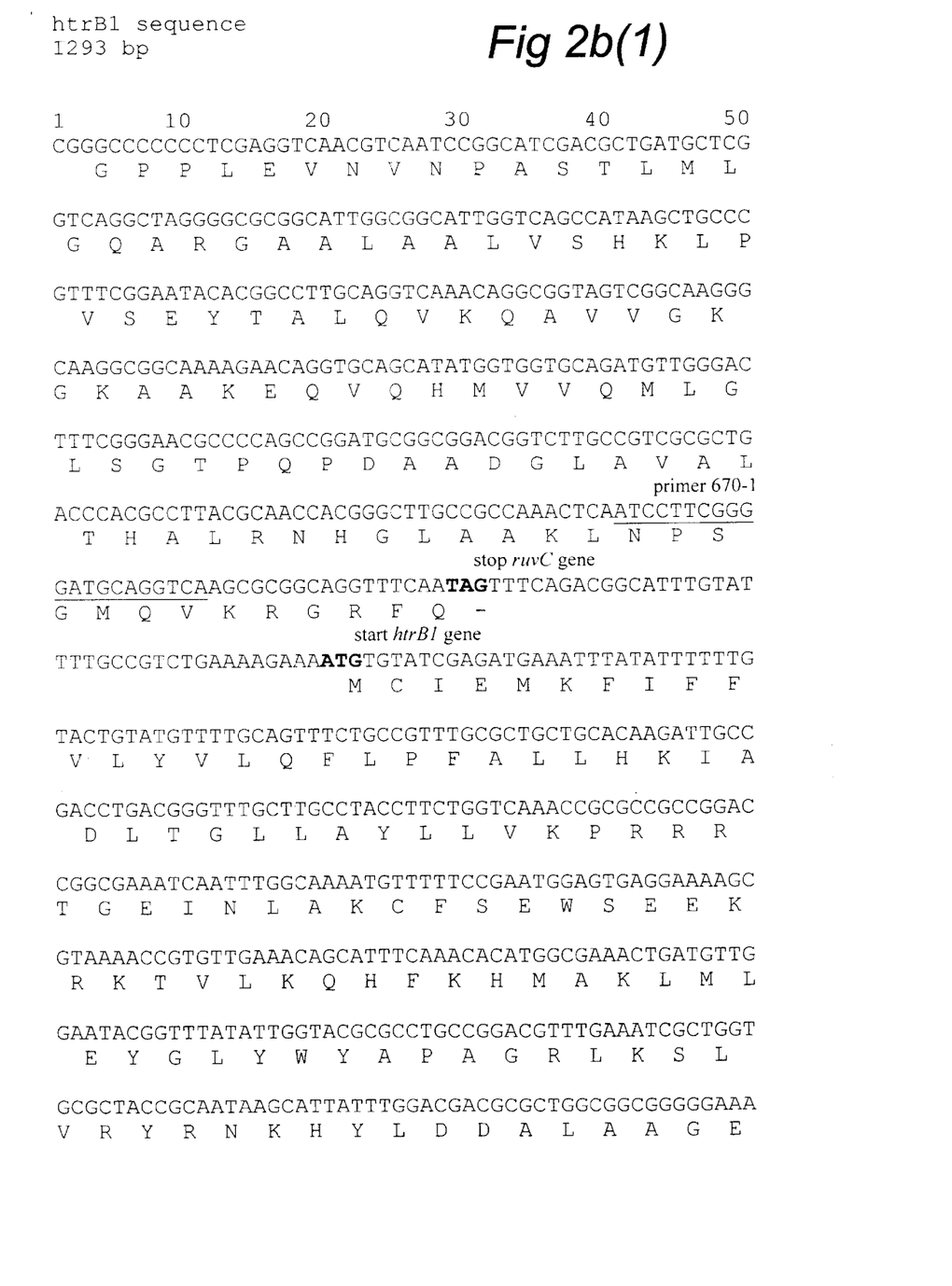
Figure 3:
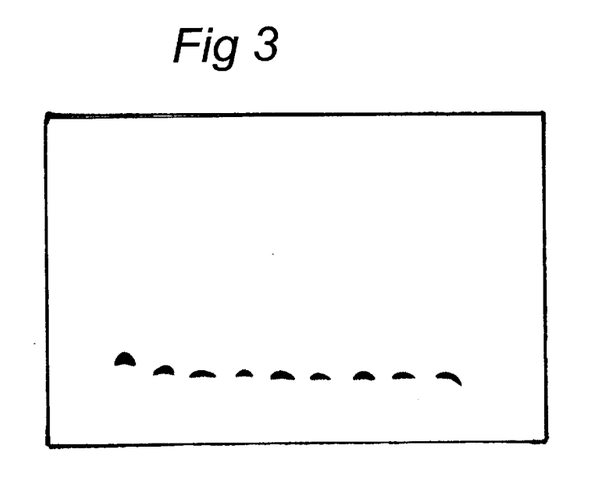
FIG. 3. Tricine-SDS-PAGE analysis of LPS from H44/76 wildtype and kanamycin-resistant transformants obtained with plasmid pBSNK6
Figure 4A:
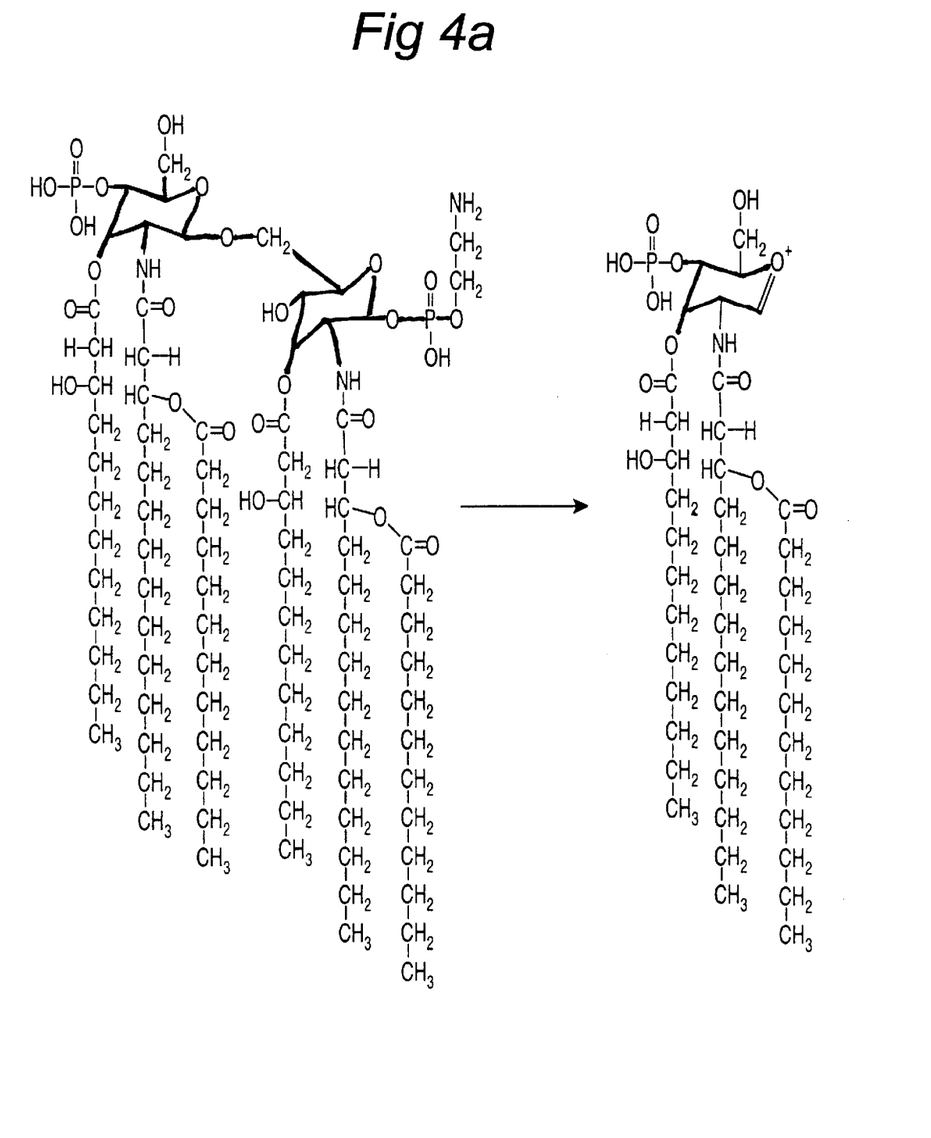
FIG. 4. Structural analysis by mass spectrometry of lipid A from H44/76 wildtype (A) and the htrB1 mutant (B)
Figure 4B:
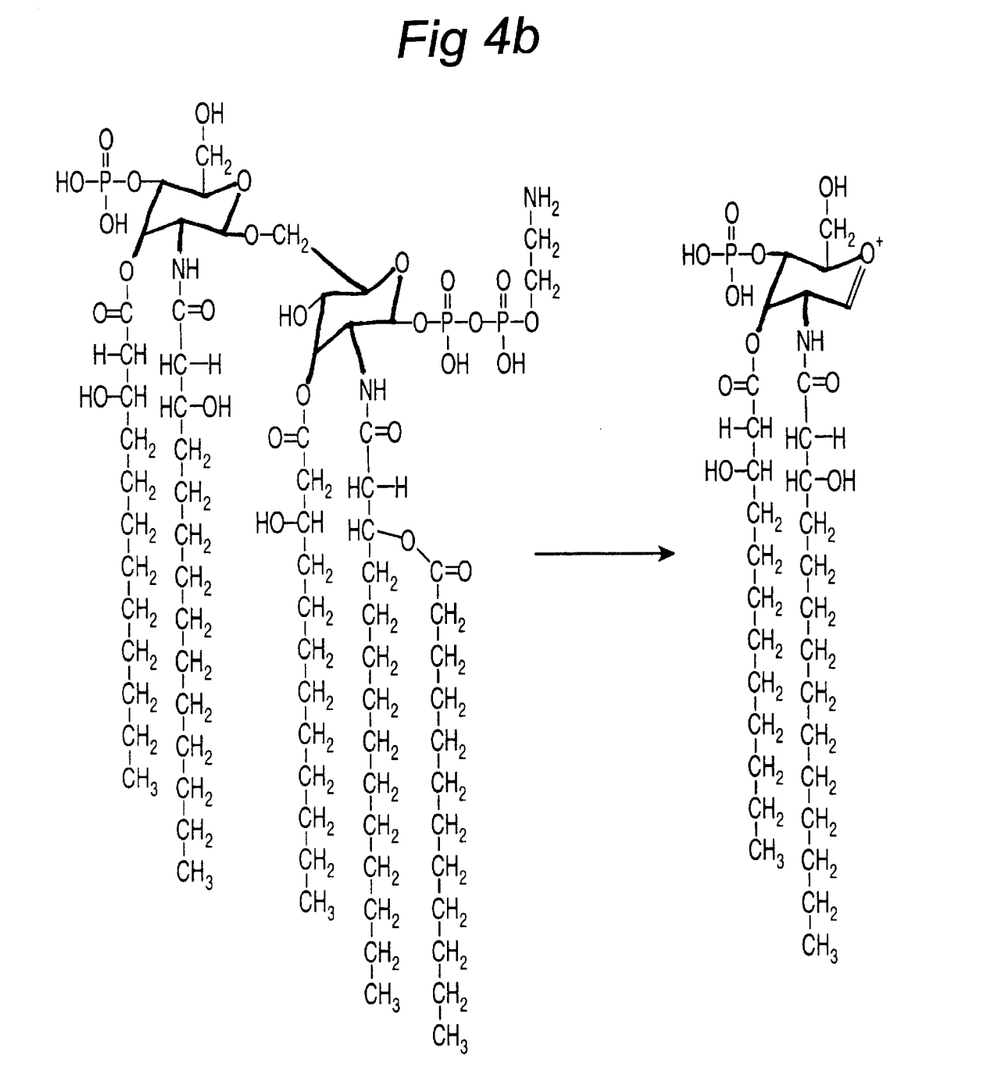
Figure 5:
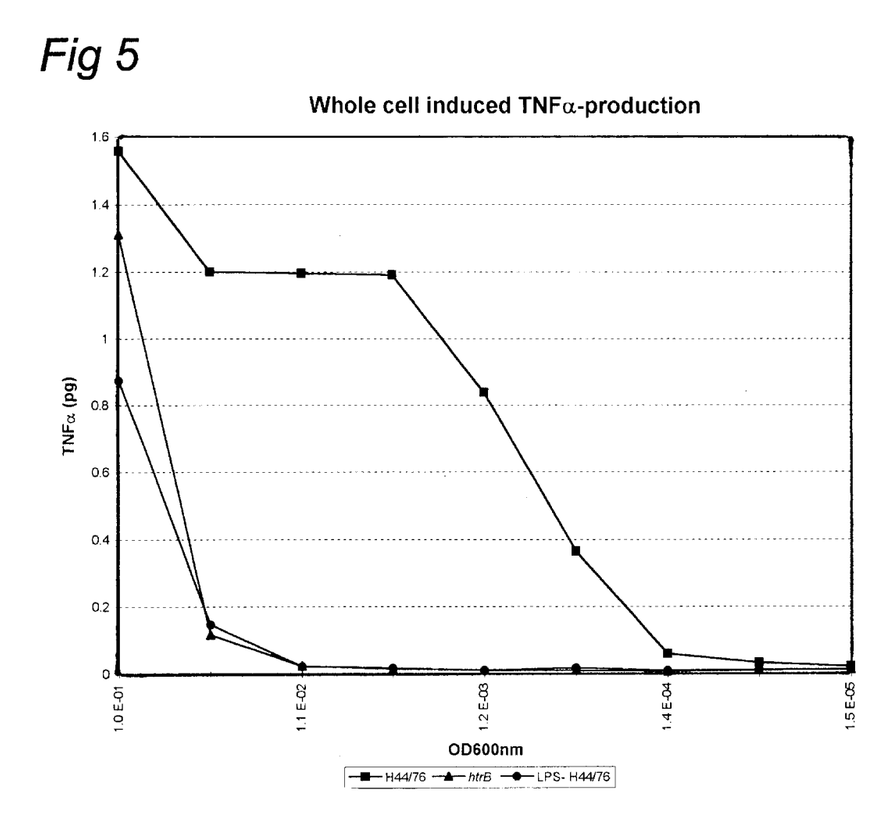
FIG. 5. TNF-a induction in MM6 cells by whole bacteria of strain H44/76, mutant htrB1 and LPS-deficient strain pLAK33.
Figure 6:
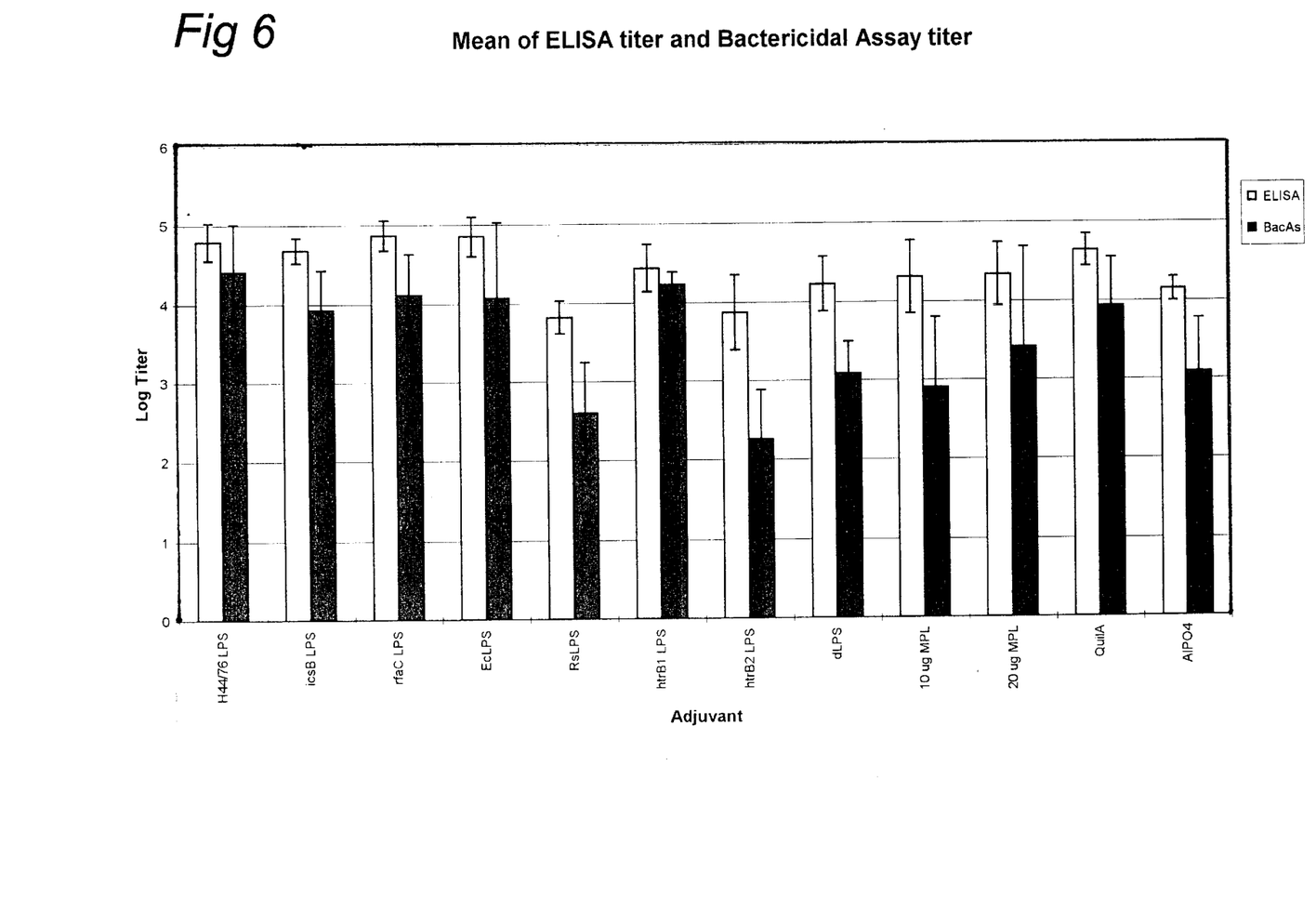
FIG. 6. Comparison of adjuvant activity of various LPS preparations when used for immunization of mice together with LPS-deficient OMCs.

Genes involved in lipid A acyloxyacylation are known in the art. Recently two late functioning acyltransferases of lipid A biosynthesis in Escherichia coli were identified as the products of the htrB and msbB genes (Clementz et al., 1996,1997); the hrtB gene was previously described as required for growth on rich media above 33° C., and the msbB gene as a multicopy suppressor of htrB. In the optimal reaction, HtrB transfers laurate to (KDO)2-lipid IVA, after which MsbB can add myristate to complete lipid A acylation (FIG. 1). The predominant products formed by htrB and msbB mutants are tetra- and penta-acyl species, respectively. The genes display 27.5% identity; a third gene belonging to this family is also present in the E. coli chromosome, but its function in lipid A biosynthesis remains to be demonstrated.

The Haemophilus influenzae genome sequence contains both htrB and MsbB homologues; mutation in htrB is associated with modification of both phosphorylation and acylation of LPS (Lee et al., 1995), suggesting a pleiotropic effect of the loss of the acyloxyacyl chains on decoration of the oligosaccharide chain. A knockout mutation in the H. influenzae htrB gene was shown to reduce LPS-associated toxicity (Nichols et al., 1997).

Apicella (also author of the cited Lee et al document) et al also describe a htrB knockout mutant in WO97/19688. They described a H. influenzae tetra acyl mutant obtained via a mutation in htrB said mutant LPS supposedly having substantially reduced toxicity yet with retained antigenicity.

They used homology of E coli htrB sequence to find a similar sequence for Haemophilus, This similar sequence had 56% identity and 73% similarity to the E. coli htrB sequence. Mutants of H. influenzae were made and grown. Analysis of the mutant Haemophilus LPS revealed reduction in phosphoethanolamines, 50% less with two in the inner core. A species being a mono or diphosphoryl pentaacyl Lipid A of H. influenzae missing one of the secondary acyl chains (e.g. myrisitic acid moiety) in about 10% is also revealed by Apicella. In addition a tetraacyl was illustrated as having been present in about 90%. Thus the Apicella method produces a mixture of recombinant H. influenzae LPS structures wherein the majority product has no secondary acyl chains. Bactericidal assays of LOS preparations are provided by Apicella as are infant rat model and chinchilla immunisations using the mutant H. influenzae strain. The tests use LPS per se as immunogen they do not illustrate or suggest anything concerning adjuvant activity. The immune response against LPS per se is exhibited in the tests of Apicella et al.

A Salmonella mutant is also disclosed. This mutant was achieved following the method analogously to the one for H. influenzae The Salmonella mutant provides an LPS in which the 3'substitution on the N linked C14 is a C16 rather than a C12 fatty acid. This embodiment was tenfold less toxic than wild type. No details on antigenicity are provided for this substance.

They suggested the method could also be applicable to Neisseria, Moraxella, and Campylobacter. In Example 6 e.g. Apicella suggested analogous steps to the H. influenzae could be carried out for Neisseria but nothing is illustrated and the method has clearly not been carried out. To date no teaching concerning such gene in lipid A synthesis of Neisseria has been found and no details of tests wherein the gene involved in this stage of lipid A synthesis of Neisseria have been provided.

The Apicella prior art document reveals that mutation in Salmonella appears to induce another acyltransferase rather than resulting in omission of secondary acylation in contrast to the result provided for *H. influenzae*. This illustrates unpredictability in the result when mutating genes associated with lipid A synthesis in various Gram negative organisms and is in line also with the teaching of Erwin and Munford.

The Salmonella product is a hepta or hexaacyl i.e. has the same number of secondary and primary acyl chains as the non mutant. The *H. influenzae* product is in majority (90%) free of secondary acyl chains but also provides a mixture of pentacyl structures. No difference in activity is provided for any of the various structures or indicated.

The lipid A structure of *Neisseria meningitidis* had previously been analyzed by Kulshin et al in 1992. However nothing is known concerning genetic make up of Neisseria with regard to presence or absence of a htrB gene or identity thereof. In addition nothing is known of the influence any mutation in such a gene if it could be found would have on the resulting mutant strain or on the resulting product or products.

SUMMARY OF THE INVENTION

We searched for and identified a genetic sequence involved with secondary acylation of LPS. We found two different sequences in the *Neisseria meningitidis* genome. On the basis of this information i.a. we hypothesized the existence of two acyloxyacyl transferases which could work in a number of ways. One such manner could be that only one of these transferases would catalyze an addition analogous to the process of *E. coli*, i.e. HtrB (FIG. 1). Alternatively, a single enzyme might catalyze both acylations, as the meningococcal lipid A has a symmetrical structure. We thus undertook mutations in the Lipid A synthesis genes of *Neisseria meningitidis* and found that the mutant strains were viable. We also found these strains produced mutated LPS. This mutated LPS exhibited reduced toxicity. However mutation in the htrB2 gene resulted in a product that did not retain immunostimulatory activity. It resulted in a product that would not be useful in a vaccine. It resulted in a product that could not be used as an adjuvant in a vaccine.

Surprisingly we found however that mutations in the htrB1 gene of *Neisseria meningitidis*, did provide a product that was both less toxic and provided adjuvant activity. We analysed the molecular structure of the resulting products and arrived at the conclusion that corresponding molecules from other Gram negative bacteria could be useful in an analogous manner. We found that not only the toxicity but also the adjuvant activity was closely related to the structure of the molecule. In particular the secondary acyl composition was particularly relevant. We also found the phosphorylation pattern was relevant.

Thus we now provide a method to specifically produce less toxic LPS derivatives with clear adjuvant activity, said derivatives being of a nature not previously discernible from the prior art and exhibiting characteristics neither known nor predictable from the prior art.

DETAILED DESCRIPTION OF THE INVENTION

The invention is directed at novel less toxic forms of LPS that are obtained through genetically modified Gram negative bacteria. These novel LPS structures exhibit adjuvant activity.

The novel LPS structures are defined as recombinant LPS having a reduced number of secondary acyl chains per molecule of LPS vis a vis the corresponding non modified LPS molecule, said secondary acyl chains being bound to primary acyl chains, said primary acyl chains being bound to the glucosamine of said recombinant LPS molecule, said recombinant LPS being homogenous in acylation pattern. In contrast to the prior art where chemically modified LPS has been described and the genetically engineered *H. influenzae* LPS according to Apicella the novel LPS according to the invention can be obtained such that the homogeneity of the acylation pattern, specifically also the secondary acylation pattern is guaranteed. Naturally this provides a better basis for addition to a vaccine with a view to standardisation but also with a view to analysis of activity of the resulting expression product. Quite specifically a suitable LPS according to the invention is a recombinant LPS molecule having a reduced number of secondary acyl chains vis a vis the corresponding non modified LPS molecule, said secondary acyl chains being bound to primary acyl chains, said primary acyl chains being bound to glucosamine in said recombinant LPS molecule, said recombinant LPS molecule having at least one secondary acyl chain bound to a primary acyl chain attached to the glucosamine on the reducing end of said recombinant LPS molecule. A recombinant LPS according the invention in any of the embodiments provided can have the same number of primary acyl chains as the non modified LPS. A recombinant LPS according to the invention can have the same composition of primary acyl chains as the non modified LPS. By way of example a recombinant LPS according to any of the embodiments of the invention mentioned above has 2 primary acyl chains attached to the glucosamine at the reducing end per recombinant LPS molecule. In a suitable embodiment the LPS according to the invention will have a primary acyl chain present at the 3 position of the glucosamine at the reducing end per recombinant LPS molecule. Quite specifically the lauroyl acylation is the target of amendment of the recombinant LPS vis a vis the non modified LPS. Such a recombinant LPS can have a reduced number of secondary lauroyl chains per recombinant LPS molecule in comparison to the non modified LPS. Suitably a recombinant LPS according to the invention may have a reduced number of secondary lauroyl chains attached to the non reducing end of the recombinant LPS molecule per recombinant LPS molecule in comparison to the non modified LPS. An embodiment according to the invention of any of the types described above has been found suitable wherein the recombinant LPS has at least one secondary lauroyl chain attached to a primary acyl chain at the reducing end of the LPS molecule per recombinant LPS molecule. By way of example such a recombinant has a secondary lauroyl chain on the primary acyl chain at the 2 position of the glucosamine at the reducing end of the LPS molecule per recombinant LPS molecule. In particular a recombinant LPS according to any of the preceeding embodiments, said recombinant LPS having a secondary acyl chain on the primary acyl chain at the 2 position of the glucosamine at the reducing end of the LPS molecule per recombinant LPS molecule has in fact been found to be of interest. Another embodiment of interest is a recombinant LPS molecule according to any of the above definitions of the invention has 5 acyl chains in toto per recombinant LPS molecule. In an alternative suitable embodiment the recombinant LPS according to the previous embodiments of the invention has a phosphate group attached to the glucosamine at the non reducing end of the LPS molecule and a phosphate group attached to the glucosamine at the reducing end of the molecule per recombinant LPS molecule. In addition to the above a further embodiment of the invention consists of a recombinant LPS with one phosphoethanolamine group per recombinant LPS molecule. Also a feasible LPS according to the invention has one phosphoethanolamine group per recombinant LPS molecule. A recombinant LPS having a phosphate group attached to the glucosamine at the non reducing end of the LPS molecule and a phosphate group attached to the glucosamine at the reducing end of the molecule, the latter phosphate group further being attached to phosphoetlhaniolaminie at the reducing end of the molecule per recombinant LPS molecule forms a particularly suitable embodiment. Note that any combination of the described elementd of the various LPS embodiments are also considered to fall within the scope of the invention. Any Gram negative bacterium can serve as source for a recombinant LPS according to the invention. Specifically in this respect a bacterium selected from the group consisting of the following bacteria Neisseria, Bordetella, Salmonella and Haemonhilus is considered a suitable source. The Neisseria and Bordetella organisms are particularly damaging and LPS derived from such bacteria are preferred. *Neisseria meningitidis* and *Neisseria gonorrhoae* are two suitable candidates from the bacteria belonging to the group of bacteria falling within the definition of Neisseria, In the examples we have used LPS derived from the *Neisseria meningitidis* strain H44/76. On the basis of this strain we found the following LPS structure to be extremely useful.

As stated the recombinant LPS according to the invention exhibits reduced toxicity. THe reduced toxicity can be deteremined using common assays for toxicity of which a number are provided in the examples but of which any number of others will be apparent to a person skilled in the art. A recombinant LPS according to any of the embodiments of the invention will exhibit reduced toxicity vis a vis the corresponding non modified LPS. Another substance against which the reduced toxicity can be tested is MPL when tested using corresponding assays. A recombinant LPS according to any of the embodiments of the invention exhibits adjuvant activity. A substance against which the adjuvant activity can be compared is MPL when tested using corresponding assays. A recombinant LPS according to the invention exhibits adjuvant activity higher than that of MPL when tested using corresponding assays. Alternatively the adjuvant activity can be compared to that of *Rhodobacter sphaeroides* LPS and when tested using corresponding assays the LPS according to the invention will show higher adjuvant activity. Another way to test the adjuvant activity of a recombinant LPS according to the invention is against alkaline hydrolyzed meningococcal LPS. A suitable recombinant LPS according to the invention will exhibit adjuvant activity higher than that of alkaline hydrolyzed meningococcal LPS when tested using corresponding assays. The adjuvant activity can be assessed with an antigen directed against the same bacterial group from which the non modified LPS was derived. The adjuvant activity can also be assessed with an antigen directed against a different organism than one belonging to the bacterial group from which the non modified LPS was derived. The examples provide illustration of a test of adjuvant activity. The recombinant LPS according to the invention can be substantially isolated and purified using standard methodologies for isolating LPS from bacterial cultures.

The subject invention is not only directed at the LPS per se as defined in any of the aforementioned embodiments of recombinant LPS according to the invention but also at a composition comprising such recombinant LPS. Such a composition can be a composition for stimulating immune reaction. Quite specifically such a composition can be a vaccine with the recombinant LPS as active component in combination with a pharmaceutically acceptable carrier. A composition according to the invention and specifically a vaccine according to the invention comprises the recombinant LPS as adjuvant. The composition is preferably for stimulating immune reaction against a Gram negative bacterium. The composition can be used for combating infections caused by organisms other than the organism corresponding to that from which the LPS corresponding to that of the recombinant LPS was derived. However it can quite suitably be used for combating the same type of organism. A Neisseria LPS can be used in a vaccine combating a Neisseria infection but also for combating a Bordetella infection. It is also envisaged that a vaccine against measles could comprise a recombinant LPS according to the invention as an adjuvant. A composition according to the invention can be free of other adjuvants. Specifically a composition according to the invention, preferably a vaccine is free of any of the commonly used adjuvants of commercial vaccines. Suitably a composition according to the invention is free of the following adjuvants Freund type mineral oil emulsions, aluminium salts, saponins, muramyl dipeptide and derivatives MPL and MF59. Alternatively a vaccine according to the invention comprises the commonly used commercial adjuvants in lower dosages than is currently in practice for commercial vaccine preparations thus exhibiting lower toxicity than the corresponding vaccine without the LPS according to the invention and the normal adjuvant composition and amount. For a composition according to the invention to have imune stimulatory action and to be useful as a vaccine it is preferable the composition comprises an antigen in addition to the adjuvant for stimulating immune reaction. Suitably the antigen is specific for obtaining stimulating immune reaction against an organism other than the organism corresponding to that from which the LPS corresponding to that of the recombinant LPS was derived. It is also an embodiment that a composition according to the invention comprises an antigen in addition to the adjuvant for stimulating immune reaction, said antigen being specific for obtaining stimulating immune reaction against an organism corresponding to the group of organisms from which the LPS corresponding to that of the recombinant LPS was derived. By way of example a Neisseria antigen and a recombinant Neisseria LPS according to the invention. This need not necessarily be the same species but they can be. So a *Neisseria meningitidis* recombinant LPS can be present together with a *Neisseria meningitidis* antigen. However the LPS can also be derived from *Neisseria gonorrhoeae* or from a Bordetella species. Suitably a composition according to the invention will be in a medicinal dosage form. For example an injectible dosage form. Preferably the composition according to the invention will occur in a systemically acceptable form. The adjuvant and any additional antigen will be present in amounts suitable for providing immune stimulatory reaction in a human or animal. It will be present in a non toxic amount or in a tolerably toxic amount. It is preferred application of the vaccine does not provide side effects of a distressing nature. The invention also comprises the use of a recombinant LPS according to any of the embodiments of the invention as adjuvant in a composition for stimulating immune reaction specifically in a vaccine formulation. The invention also covers a method of treatment for stimulating the immune system of a human or animal by administration of a recombinant LPS or composition comprising such in any of the embodiments described for a composition according to the invention in a dosage sufficient to provide immune stimulation. a person skilled in the art of vaccines will be able to ascertain on the basis of the subject and/or disease or infection to be combated what formulations and dosage regimes can be applied. Commonly available antigens and vaccine carriers can be used analogously to known vaccines. A buffer solution is a suitable example of a carrier. The method of administration can be by means of any common method for example parenteral (e.g. intravenous or intramuscular) or oral (e.g. using typhoid bacterial cells to encapsulate the active substance(s)) administration.

The subject invention also provides a method for producing a recombinant LPS according to the invention. The method comprises culturing a recombinant Gramnegative bacterium, said recombinant gram negative bacterium comprising a mutation in the lipid A synthesis route at the level of addition of secondary acyl chains to the primary acyl chains attached to the glucosamine of the LPS molecule followed by optionally isolating and purifying the resultant LPS. Specifically the mutation is a mutation in a gene encoding an enzyme associated with secondary acyl addition. As disclosed above a number of synthesis routes are available in the art for various Gram negative bacteria. Using the data present in the prior art in combination with the subject matter disclosed in the subject document one can arrive at various methods for various sGram negative organisms to provide a recombinant LPS according to the invention. Using the sequence data for htrB provided for *Neisseria meningitidis* strain H44/76 one can arrive at corresponding sequences in other organisms e.g. other Neisseria. Introduction of a mutation eliminating expression of an active htrB1 expression product in such organism will ensure production of the desired recombinant LPS. The location and identification of the htrB1 gene is provided in detail in the examples for *Neisseria meningitidis* strain H44/76. The sequence data generated can be extrapolated to other strains. Using available sequence data and homology of the probe used in the example or taking another probe on the basis of the whole or partial encoding sequence of *Neisseria meningitidis* strain H44/76 htrB1 can lead to indication of alternative htrB sequences in other organisms. In addition to the above for the Neisseria organisms htrB1 has been found to be located downstream of the ruvc gene thus any gene sequence encoding htr downstream of a ruvc sequence is a suitable location for introducing a mutation. Any gene sequence exhibiting more than 33% homology to the encoding sequence of FIG. 2 in a Gram negative organism is a potential location for mutation to provide a recombinant LPS according to the invention. Preferably the degree of homology is even higher e.g. higher than 50% preferably higher than 60%. The closer the homology is to 100% over a stretch of at least 500 bp and more preferably over the whole length of the coding sequence the better. Alternatively or in combination one can search for an encoding sequence of the same or close amino acid sequence and mutate the corresponding sequence such that no active expression product is produced. Quite suitably the sequence is located downstream of a ruvc sequence. Preferably the mutation of choice is a mutation in a gene encoding an enzyme associated with secondary acyl addition to primary acyl chains at the reducing end of the LPS. As is apparent from the examples this can suitably be a mutation in a gene encoding an enzyme associated with secondary lauroyl addition. A specific suitable mutation is in a gene encoding an enzyme associated with secondary acyl chain addition at the primary acyl chain present at the 2' position of the glucosamine at the non reducing end of the LPS molecule.

In an embodiment according to the invention the recombinant LPS is isolated and purified such that it is free of any other forms of LPS. In a method of formulating a vaccine it is preferred to first isolate the LPS in order for exact formulation of the vaccine to be achieved. Suitably a method according to the invention consists of providing a recombinant LPS having a reduced number of secondary lauroyl chains per recombinant LPS molecule in comparison to the non modified LPS which recombinant LPS is isolated and purified such that it is free of any other forms of LPS. In a preferred embodiment the recombinant LPS is provided that has a reduced number of secondary lauroyl chains attached to the non reducing end of the recombinant LPS molecule per recombinant LPS molecule in comparison to the non modified LPS. In a preferred embodiment the recombinant LPS is provided that has at least one secondary lauroyl chain attached to a primary acyl chain at the reducing end of the LPS molecule per recombinant LPS molecule. Suitably in such a method the mutation can be such that the recombinant LPS has a secondary acyl chain on the primary acyl chain at the 2 position of the glucosamine at the reducing end of the LPS molecule per recombinant LPS molecule. Suitably the secondary acyl chain is a secondary lauroyl chain. A preferred method involves a mutation process resulting in a recombinant LPS according to the invention having 5 acyl chains in toto per recombinant LPS molecule. An alternative method of the invention consists of producing a recombinant LPS having a phosphate group attached to the glucosamine at the non reducing end of the LPS molecule and a phosphate group attached to the glucosamine at the reducing end of the molecule per recombinant LPS molecule. Suitably the LPS product is isolated and purified such that it is free of any other forms of LPS. Alternatively the method can comprise producing a recombinant LPS having one phosphoethanolamine group per recombinant LPS molecule which suitably is isolated and purified such that it is free of any other forms of LPS.

A method wherein the recombinant LPS having a phosphate group attached to the glucosamine at the non reducing end of the LPS molecule and a phosphate group attached to the glucosamine at the reducing end of the molecule, the latter further being attached to the phosphoethanolamine at the reducing end of the molecule per recombinant LPS molecule is produced and preferably is isolated and purified such that it is free of any other forms of LPS is provided by the invention.

The invention is further illustrated by the examples which are not to be considered a restriction on the scope of the invention. The numerous variants of the LPS and uses thereof according to the invention will be apparent to a person skilled in the art on the basis of information provided in the claims, description and figures in combination with common general knowledge in the field of genetic engineering, specifically of Gram negative bacteria and vaccine production. Specifically the references cited and information in the DNA databases accessible to the public with Gram negative genomic sequences accessible prior to the filing date are incorporated herein by reference. Where methods or processes of isolation, purification are mentioned such are common in the art and analogous to other well known procedures. The same comment is valid for introducing a mutation in the htrB1 gene. This can occur via insertion, deletion or substitution in a manner known per se once a DNA sequence of choice to be mutated has been located in an organism. The method of formulation of a vaccine and administration thereof are also common procedures that need no further elucidation. The terms used are art recognised terms for a person skilled in the art that can be derived from general text books concerning the field of genetic engineering, Gram negative bacteria and immunology and/or from the cited references.

EXAMPLE 1
Construction of *Neisseria Meningitidis* Mutant htrB 1 with Altered Lipid A Using the htrB/msbB gene sequences from *Escherichia coli* and *Haemophilus influenzae*, we performed a BLAST search on the gonococcal genome sequences made available on the Internet by the University of Oklahoma. Several contigs with significant homology were identified, and PCR primers were designed based on these sequences. With meningococcal chromosomal DNA as template, primers pr447-2 and pr670-1 gave a ca. 500 bp PCR product which upon cloning in vector pCRII and sequencing was found to be homologous to htrB/msbB sequences from several bacterial species (33% and 31% respectively for the *E. coli* genes). This fragment was used as probe for isolation of a larger chromosomal fragment containing the complete htrB1 gene of *Neisseria meningitidis* (FIG. 2). Immediately upstream of this gene an open reading frame with homology to the ruvC gene from *E. coli* was found, which presumably is involved in DNA repair and recombination and not LPS biosynthesis.

A kanamycin-resistance cassette was inserted into the BglI site located within the cloned htrB1 PCR product, and the resulting construct (plasmid pBSNK6, containing also the neisserial uptake sequence) was used to transform meningococcal strain H44/76 to kanamycin resistance. PCR was used to verify that correct allelic exchange with the chromosomal htrB1 gene had occurred. All transformants thus obtained showed an increased mobility of their LPS when analysed by Tricine-SDS-PAGE followed by silver staining (FIG. 3).

Binding of monoclonal antibodies specific for the oligosaccharide part of meningococcal LPS was not affected by the mutation, suggesting that only the lipid A part must have been altered.

EXAMPLE 2

Structural Analysis of HtrB1 Mutant Lipid A

Fatty acid analysis by gas chromatography/mass spectrometry of whole cells showed a reduced ratio of C12:0/C12:0 3-OH in the htrB1 mutant as compared to the wildtype parent strain, indicating a (partial) loss of the secondary C12:0 acyl chain(s). LPS from this mutant was purified through hot phenol/water extraction, and the lipid A fraction was obtained after acid hydrolysis and chloroform/methanol extraction. Its structure was subsequently investigated using tandem mass spectrometry. The analysis revealed a major penta-acyl species in which the C12:0 acyloxyacyl chain was missing from the nonreducing end of the molecule (FIG. 4).

An additional difference from the parent strain is found in the phosphorylation pattern at the reducing end of the disaccharide, where an additional phosphate group is present. This mutant lipid A molecule has a unique structure not found in any of the mutants described previously for other Gram-negative bacteria.

EXAMPLE 3

Biological Activity of HtrB1 Mutant LPS

Whole cells from mutant strain htrB1 were tested for their LPS-associated biological activity by both the Limulus amebocyte lysate (LAL) and tumor necrosis factor-a) (TNF-a) induction assays. In the LAL assay, a 7-fold reduction in activity was observed for whole cells from the mutant as compared to the wildtype. For TNF-a induction by MM6 cells, htrB1 bacterial cells showed at least a 100-fold reduction in activity as compared to the wildtype, similar to the reduction previously found for whole cells of a completely LPS-deficient mutant (FIG. 5) (L. Steeghs et al 1998). Immunization of mice with outer membrane complexes isolated from the LPS-deficient meningococcal mutant was used to compare the adjuvant activity of various LPS preparations. Antibody responses were measured in whole-cell ELISA and bactericidal assay against parent strain H44/76.

Immunogenicity of the major outer membrane proteins was restored to normal levels by both wildtype and htrB1 mutant LPS, but less so by the atoxic LPS species monophosphoryl lipid A (MPL), *Rhodobacter sphaeroides* LPS and alkaline-hydrolysed meningococcal LPS (FIG. 6) (Nakano M. and Matsuura M.). Thus, the htrB1 mutant LPS has retained adjuvant activity in spite of decreased toxicity.

EXAMPLE 4

Properties of the HtrB2 Lipid A Mutant

Another gene with homology to htrB/msbB from *E. coli* and *H. influenzae* was similarly identified and inactivated as in the preceeding examples for htrB1. In contrast to htrB1 however, LPS from this mutant (termed htrB2) has strongly reduced adjuvant activity as well as reduced toxicity (FIG. 6). Also in contrast with htrB1, this mutation could not be introduced into strain H44/76 with wildtype LPS but only into a galE derivative with a galactose-deficient, truncated oligosaccharide chain.

METHODS

Bacterial Strains and Plasmids

The *E. coli* strains NM522 and INVaF' were grown on LB medium at 37° C. The *N. meningitidis* strain H44/76 and its derivatives were grown at 37° C. on GC medium base (Difco) supplemented with IsoVitaleX (Becton Dickinson) in a humid atmosphere containing 5% CO2, or in liquid medium as described previously (van der Ley et at., 1993). For selection of meningococcal transformants (van der Ley et al., 1996) kanamycin was used in a concentration of 75–100 microgrammes/ml. With *E. coli*, antibiotics were used in the following concentrations: ampicillin, 100 microgrammes/ml; kanamycin, 100 microgrammes/ml. For cloning of PCR fragments, the TA cloning kit with the vector pCRII (Invitrogen) was used.

Recombinant DNA Techniques

Most recombinant DNA techniques were as described in Sambrook et al.(1989). Plasmid DNA was isolated using the pLASmix kit (Talent). The polymerase chain reaction (PCR) was performed on a Perkin Elmer GeneAmp PCR system 9600 with Taq polymerase. Sequence analysis was performed with an Applied Biosystems automatic sequencer on double-stranded plasmid DNA templates (isolated with Qiagen columns) and with a cycle sequencing protocol.

LPS Analysis

Tricine-sodium dodecyl sulphate polyacrylamide gel electrophoresis was performed in 4% stacking and 16% separating gels as described by Lesse et al. (1990). Proteinase K-treated, boiled bacterial cells were used as samples. The gels were run for 17 h at a constant current of 20 mA, and silver stained by the method of Tsai and Frasch (1982). The chromogenic LAL assay for endotoxin activity was performed using the QCL-1000 kit from BioWhittaker Inc. (Walkersville, Md., USA) according to the instructions of the manufacturer. Overnight cultures were diluted in meningococcal medium to an OD at 620 nm of 0.1, and serial dilutions of these stocks were used as samples in the LAL assay, TNF-a induction by bacterial suspensions was tested with the human macrophage cell-line MM6 and quantitated from culture supernatants using the TNF-a sensitive cell line WEHI 164 (Espevik and Nissen, 1986). For fatty acid analysis by GC-MS, OMC samples were acetylated for 3 h at 900C in pyridine and acetic acid anhydride in order to completely dissolve the LPS. The samples were subsequently heated for 3 h at 650C in tetrahydrofuran in the presence of $LiAlH_4$ to reduce the O-linked fatty acids to the free alcohols. These were derivatized to TMS-ethers for 1 h at 600C with BSTFA+1% TMCS in pyridine, and analyzed by GC-MS on an Autospec (Micromass, Man-ches-ter, UK) in the electron impact mode. The amount of 3-OH C12 in the samples was quantified using 2-OH C12 as internal standard. LPS was isolated by the hot phenol-water extraction method (Westphal and Jann, 1965). For isolation of lipid A, LPS was subjected to mild acid hydrolysis (1% acetic acid, 2.5 h 1000C), followed by precipitation and final fractionation in chloroform-methanol-water. Structural analysis of purified lipid A was performed with electrospray tandem mass spectrometry. Mass spectrometry was carried out on a quadrupole ion trap instrument (LCQ Finnigan Corp. San Jose USA) fitted with a nanoelectrospray ion source operated at 600 V. The temperature of the inlet capillary was set at 200° C., the maximum number of ions in the trap at $1,0 \times 10^7$ and the maximum injection time at 150 ms. Nanoelectrospray needles were filled with 2 microlitres of sample solution. Full MS spectra were recorded over the range 150–1850 amu. Full MS(n) spectra were always preceded by a zoom scan of the parent ion to determine the m/z ratio of the parent more accurately as well asto determine its charge state. MS/MS spectra were recorded with a window for parent ion selection of 3 amu. The excitation energy was adjusted until the intensity ratio of the base peak to the parent was between 5 and 20. Except for zoom scans spectra were recorded in centroid mode.

Characterization of OMC Composition

Binding of mAbs specific for class 1, 3 and 4 OMPs and for the oligosaccharide part of immunotype L3 LPS was tested in a whole-cell ELISA (van der Ley et al., 1995, 1996). Isolation of OMCs by sarkosyl extraction and their analysis by SDS-PAGE were done as described previous-ly (van der Ley et al., 1993).

Immunization of Mice

Six to eight-weeks old BalB/C mice, five animals each group, were immunized on day 0 subcutaneously with 20 microgrammes LPS-deficient H44/76 OMCs supplemented with adjuvant and dissolved in 0.5 ml PBS. At day 14 and day 28 immunization was repeated and mice were bled at day 42. Sera were collected and stored at 4° C. The serum bactericidal activity against strain H44/76 was assayed as described in Hoogerhout et al. (1995), using a final concentration of 20% rabbit complement. The bactericidal titer was measured as the reciprocal serum dilution showing more than 90% killing.

REFERENCES

Clementz, T., Bednarski, J. J. and Raetz, C. R. H.: Function of the htrB high temperature requirement gene of *Escherichia coli* in the acylation of lipid A. J. Biol. Chem. 271 (1996) 12095–12102.

Clementz, T., Zhou, Z. and Raetz, C. R. H.: Function of the *Escherichia coli* msbB gene, a multicopy suppressor of htrB knockouts, in the acylation of lipid A. J. Biol. Chem. 272 (1997) 10353–10360.

Espevik, T. and Nissen, M. J.: A highly sensitive cell line, WEHI 164 clone 13, for measuring cytotoxic factor/tumor necrosis factor from human monocytes. J. Immunol. Methods 95 (1986) 99–105.

Hoogerhout, P., Donders, E. M. L. M., van Gaans-van den Brink , J. A. M., Kuipers, B., Brugghe, H. F., van Unen, L. M. A., Timmernans, H. A. M., ten Hove, G. J., de Jong, A. P. J. M., Peeters, C. C. A. M., Wiertz, E. J. H. J. and Poolman, J. T. Conjugates of synthetic cyclic peptides elicit bactericidal antibodies against a conformational epitope on a class 1 outer membrane protein of *Neisseria meningitidis*. Infect. Immun. 63 (1995) 3473–3478. Kulshin, V. A., Z\'e4hringer, U., Lindner, B., Frasch C. E., Tsai, C., Dimitriev, A. and Rietschel, E. T.: Structural characterization of the lipid A component of pathogenic *Neisseria meningitidis*. J. Bacteriol. 174 (1992) 1793–1800.

Lee, N. G., Sunshine, M. G., Engstrom, J. J., Gibson, B. W. and Apicella, M. A.: Mutation of the htrB locus of *Haemophilus influenzae* nontypable strain 2019 is associated with modifications of lipid A and phosphorylation of the lipo-oligosaccharide. J. Biol. Chem. 270 (1995) 27151–27159.

Lesse, A. J., Campagnari, A. A., Bittner, W. E. and Apicella, M. A.: Increased resolution of lipopolysaccharides and lipooligosaccharides utilising tricine-sodium dodecyl sulfate-polyacrylamide gel electrophoresis. J. Immunol. Meth. 126 (1990) 109–117. van der Ley, P., van der Biezen, J., Hohenstein, P., Peeters, C. and Poolman, J. T.: Use of tran-sfor-ma-tion to construct antigenic hybrids of the class 1 outer membrane protein in *Neisseria meningitidis*. Infect.Immun. 61 (1993) 4217–4224.

van der Ley, P., van der Biezen, J. and Poolman, J. T.: Construction of *Neisseria meningitidis* strains carrying multiple chromosomal copies of the porA gene for use in the production of a multivalent outer membrane vesicle vaccine. Vaccine 13 (1995) 401–407.

van der Ley, P., Kramer, M., Steeghs, L., Kuipers, B., Andersen, S. R., Jennings, M. P., Moxon, E. R. and Poolman, J. T.: Identification of a locus involved in meningococcal lipopolysaccharide biosynthesis by deletion mutagenesis. Mol. Microbiol. 19 (1996) 1117–1125.

Nakano, M. and Matsuura M. in The Theory and Practical Application of Adjuvants D. E. S. Stewart-Tull ed. John Wiley & Sons 1995 Chapter 14, p315–336.

Nichols, W. A., Raetz, C. R. H., Clementz, T., Smith, A. L., Hanson, J. A., Ketterer, M. R., Sunshine, M. and Apicella, M. A.: htrB of *Haemophilus influenzae*: determination of biochemical activity and effects on virulence and lipooligosaccharide toxicity. J. Endotoxin Res. 4 (1997) 163–172.

Sambrook, J., Fritsch, E. F. and Maniatis, T.: Molecular Cloning: A Laboratory Manual. Cold Spring Harbor Laboratory Press, Cold Spring Harbor, New York, 1989.

Steeghs, L., den Hartog, R., den Boer, A., Zomer, B., Roholl, P. and van der Ley P. Nature 392: 449–450 (1998).

Tsai, C. M. and Frasch, C. E.: A sensitive silver stain for detecting lipopo-lysaccharides in polyacrylamide gels. Anal. Biochem. 119 (1982) 115–119.

Westphal, O. and Jann, J. K.: Bacterial lipopolysaccharide extraction with phenol-water and further application of the procedure. Methods Carbohydr. Chem. 5 (1965) 83–91.

What is claimed is:

1. Lipopolysaccharide (LPS) with a lipid A having a secondary acyl chain only on a primary acyl chain at the reducing end of the glucosamine disaccharide.

2. LPS according to claim 1, wherein the lipid A has a secondary acyl chain on one of the primary acyl chains at the reducing end of the glucosamine disaccharide.

3. LPS according to claim 1, wherein the lipid A has a secondary acyl chain on the primary acyl chain at the 2 position of the glucosamine at the reducing end of the glucosamine disaccharide.

4. LPS according to claim 1, wherein the secondary acyl chain is a lauroyl chain.

5. LPS according to claim 1, with a lipid A having a phosphoethanolamine attached to a phosphate group at the reducing end.

6. LPS according to claim 1, with a lipid A having the molecular structure:

7. A composition comprising LPS as defined in claim 1.

8. A composition according to claim 7 further comprising a pharmaceutically acceptable carrier.

9. A composition according to claim 7 comprising an antigen in addition to the LPS.

* * * * *

SEQUENCE LISTING

```
<160> NUMBER OF SEQ ID NOS: 5

<210> SEQ ID NO 1
<211> LENGTH: 1293
<212> TYPE: DNA
<213> ORGANISM: Neisseria meningitidis

<400> SEQUENCE: 1 cgggccccccc ctcgaggtca acgtcaatcc ggcatcgacg ctgatgctcg gtcaggctag      60
gggcgcggca ttggcggcat tggtcagcca taagctgccc gtttcggaat acacggcctt     120
gcaggtcaaa caggcggtag tcggcaaggg caaggcggca aaagaacagg tgcagcatat     180
ggtggtgcag atgttgggac tttcgggaac gccccagccg gatgcggcgg acggtcttgc     240
cgtcgcgctg acccacgcct tacgcaacca cgggcttgcc gccaaactca atccttcggg     300
gatgcaggtc aagcgcggca ggtttcaata gtttcagacg gcatttgtat tttgccgtct     360
gaaaagaaaa tgtgtatcga gatgaaattt atatttttg tactgtatgt tttgcagttt     420
ctgccgtttg cgctgctgca caagattgcc gacctgacgg gtttgcttgc ctaccttctg     480
gtcaaaccgc gccgccggac cggcgaaatc aatttggcaa aatgttttc cgaatggagt     540 gaggaaaagc gtaaaaccgt gttgaaacag catttcaaac acatggcgaa actgatgttg     600
gaatacggtt tatattggta cgcgcctgcc ggacgtttga aatcgctggt gcgctaccgc     660
aataagcatt atttggacga cgcgctggcg gcggggggaaa aagtcatcat cctgtatccg     720
cacttcaccg cgttcgagat ggcggtgtac gcgcttaatc aggatatccc gctgatcagt     780
atgtattccc atcaaaaaaa caagatattg gacgaacaga ttttgaaagg ccgcaaccgc     840
tatcacaacg tcttccttat cgggcgcacc gaagggctgc gcgccctcgt caaacagttc     900
cgcaaaagca gcgcgccgtt tctgtatctg cccgatcagg atttcggacg caacgattcg     960 gttttgtgg atttttcgg tattcagacg gcaacgatta ccggattgag ccgcattgcc    1020
gcgcttgcaa atgcaaaagt gatacccgcc attcccgtcc gcgaggcaga caatacggtt    1080
acattgcatt tctaccctgc ttggaaatcc tttccgggtg aagacgcgaa agccgacgcg    1140
cagcgcatga accgttttat cgaagacagg gtgcgcgaac atccggaaca atattttgg     1200 ctgcacaagc gttttaaaac ccgtccggaa ggcagccccg attttactg actacgtaaa    1260 attacaaaac atatcaggcg tttcagatca aaa                                1293

<210> SEQ ID NO 2
```

```
<211> LENGTH: 310
<212> TYPE: PRT
<213> ORGANISM: Neisseria meningitidis

<400> SEQUENCE: 2

Met Cys Ile Glu Met Lys Phe Ile Phe Phe Val Leu Tyr Val Leu Gln
 1               5                  10                  15

Phe Leu Pro Phe Ala Leu Leu His Lys Ile Ala Asp Leu Thr Gly Leu
            20                  25                  30

Leu Ala Tyr Leu Leu Val Lys Pro Arg Arg Thr Gly Glu Ile Asn
        35                  40                  45

Leu Ala Lys Cys Phe Ser Glu Trp Ser Glu Glu Lys Arg Lys Thr Val
    50                  55                  60

Leu Lys Gln His Phe Lys His Met Ala Lys Leu Met Leu Glu Tyr Gly
65                  70                  75                  80

Leu Tyr Trp Tyr Ala Pro Ala Gly Arg Leu Lys Ser Leu Val Arg Tyr
                85                  90                  95

Arg Asn Lys His Tyr Leu Asp Asp Ala Leu Ala Ala Gly Glu Lys Val
            100                 105                 110

Ile Ile Leu Tyr Pro His Phe Thr Ala Phe Glu Met Ala Val Tyr Lys
        115                 120                 125

Val Ile Ile Leu Tyr Pro His Phe Thr Ala Phe Glu Met Ala Val Tyr
130                 135                 140

Asn Lys Ile Leu Asp Glu Gln Ile Leu Lys Gly Arg Asn Arg Tyr His
145                 150                 155                 160

Asn Ala Leu Asn Gln Asp Ile Pro Leu Ile Ser Met Tyr Ser His Gln
                165                 170                 175

Lys Val Phe Leu Ile Gly Arg Thr Glu Gly Leu Arg Ala Leu Val Lys
            180                 185                 190

Gln Phe Arg Lys Ser Ser Ala Pro Phe Leu Tyr Leu Pro Asp Gln Asp
        195                 200                 205

Phe Gly Arg Asn Asp Ser Val Phe Val Asp Phe Phe Gly Ile Gln Thr
    210                 215                 220

Ala Thr Ile Thr Gly Leu Ser Arg Ile Ala Ala Leu Ala Asn Ala Lys
225                 230                 235                 240

Val Ile Pro Ala Ile Pro Val Arg Glu Ala Asp Asn Thr Val Thr Leu
                245                 250                 255

His Phe Tyr Pro Ala Trp Lys Ser Phe Pro Gly Glu Asp Ala Lys Ala
            260                 265                 270

Asp Ala Gln Arg Met Asn Arg Phe Ile Glu Asp Arg Val Arg Glu His
        275                 280                 285

Pro Glu Gln Tyr Phe Trp Leu His Lys Arg Phe Lys Thr Arg Pro Glu
    290                 295                 300

Gly Ser Pro Asp Phe Tyr
305                 310

<210> SEQ ID NO 3
<211> LENGTH: 109
<212> TYPE: PRT
<213> ORGANISM: Neisseria meningitidis

<400> SEQUENCE: 3

Gly Pro Pro Leu Glu Val Asn Val Asn Pro Ala Ser Thr Leu Met Leu
 1               5                  10                  15
```

```
Gly Gln Ala Arg Gly Ala Ala Leu Ala Ala Leu Val Ser His Lys Leu
            20                  25                  30

Pro Val Ser Glu Tyr Thr Ala Leu Gln Val Lys Gln Ala Val Val Gly
        35                  40                  45

Lys Gly Lys Ala Ala Lys Glu Gln Val Gln His Met Val Val Gln Met
    50                  55                  60

Leu Gly Leu Ser Gly Thr Pro Gln Pro Asp Ala Ala Asp Gly Leu Ala
65                  70                  75                  80

Val Ala Leu Thr His Ala Leu Arg Asn His Gly Leu Ala Ala Lys Leu
                85                  90                  95

Asn Pro Ser Gly Met Gln Val Lys Arg Gly Arg Phe Gln
            100                 105

<210> SEQ ID NO 4
<211> LENGTH: 21
<212> TYPE: DNA
<213> ORGANISM: Neisseria meningitidis

<400> SEQUENCE: 4
atccttcggg gatgcaggtc a                                          21

<210> SEQ ID NO 5
<211> LENGTH: 20
<212> TYPE: DNA
<213> ORGANISM: Neisseria meningitidis

<400> SEQUENCE: 5
gaacagattt tgaaaggccg                                            20
```